United States Patent [19]

Drake et al.

[11] Patent Number: 5,419,897
[45] Date of Patent: May 30, 1995

[54] IONENE POLYMERS AS ANTHELMINTICS IN ANIMALS

[75] Inventors: Kevin D. Drake, Memphis; Wallace E. Puckett, Bartlett, both of Tenn.

[73] Assignee: Buckman Laboratories International, Inc., Memphis, Tenn.

[21] Appl. No.: 44,597

[22] Filed: Apr. 9, 1993

[51] Int. Cl.⁶ .......................................... A61K 31/495
[52] U.S. Cl. .................................... 424/78.1; 424/436
[58] Field of Search ............................... 424/78.1, 438

[56] References Cited

U.S. PATENT DOCUMENTS

| | | |
|---|---|---|
| Re. 28,808 | 5/1976 | Panzer et al. . |
| 3,697,640 | 10/1972 | Grant et al. . |
| 3,738,945 | 6/1973 | Panzer et al. . |
| 3,778,476 | 12/1973 | Rembaum et al. . |
| 3,874,870 | 4/1975 | Green et al. . |
| 3,894,946 | 7/1975 | Panzer et al. . |
| 3,894,947 | 7/1975 | Panzer et al. . |
| 3,898,336 | 8/1975 | Rembaum et al. . |
| 3,930,877 | 1/1976 | Aitken . |
| 3,931,319 | 1/1976 | Green et al. . |
| 4,025,627 | 5/1977 | Green et al. . |
| 4,027,020 | 5/1977 | Green et al. . |
| 4,054,542 | 10/1977 | Buckman et al. . |
| 4,089,977 | 5/1978 | Green et al. . |
| 4,104,161 | 8/1978 | Wein . |
| 4,105,779 | 8/1978 | Kobayashi et al. . |
| 4,111,679 | 9/1978 | Shair et al. . |
| 4,147,627 | 4/1979 | Goodman . |
| 4,164,521 | 8/1979 | Goodman . |
| 4,166,041 | 8/1979 | Goodman . |
| 4,199,569 | 4/1980 | Chabala et al. . |
| 4,352,891 | 10/1982 | Quinlan . |
| 4,506,081 | 3/1985 | Fenyes et al. . |
| 4,581,058 | 4/1986 | Fenyes et al. . |
| 4,606,773 | 8/1986 | Novak . |
| 4,650,866 | 3/1987 | Rayudu . |
| 4,758,436 | 7/1988 | Caldwell et al. . |
| 4,769,155 | 9/1988 | Dwyer et al. . |
| 4,778,813 | 10/1988 | Fenyes et al. . |
| 4,839,373 | 6/1989 | Ito et al. . |
| 4,970,211 | 11/1990 | Fenyes et al. . |
| 5,051,124 | 9/1991 | Pera . |
| 5,093,078 | 3/1992 | Hollis et al. . |
| 5,128,100 | 7/1992 | Hollis et al. . |
| 5,145,643 | 9/1992 | Pziabo et al. ................. 514/840 |

FOREIGN PATENT DOCUMENTS

| | | |
|---|---|---|
| 0045655A2 | 2/1982 | European Pat. Off. . |
| 0224249A1 | 6/1987 | European Pat. Off. . |
| 0368593 | 11/1989 | European Pat. Off. . |
| 3028082 | 2/1981 | Germany . |
| 2055575 | 3/1981 | United Kingdom . |
| PCT/GB87/00561 | 2/1988 | WIPO . |

OTHER PUBLICATIONS

European Search Report.
J. R. Georgi, et al., Parasitology for Veterinarians, Fifth Edition, 1990 pp. 242–265.
B. J. Bogitsh et al., Human Parasitology, Appendix B, Current Chemotherapeutic Regimens (1990).
R. S. Morris et al., Measurement and Evaluation of the Economic Effects of Parasitic Disease, 6 Vet. Parasitology 165 (1980).
A. R. Sykes, The Effect of Subclinical Parasitism in Sheep, 102 Vet. Record 32 (1978).
T. B. Stewart et al., Performance of Pigs with Mixed Nematode Infections Before and After Ivermectin Treatment, 39 Vet. Parasitology 253 (1991).
M. J. H. Cawdery, The Effects of Fascioliasison Ewe Fertility, 132 Brit. Vet. J. 568 (1976).

(List continued on next page.)

*Primary Examiner*—Thurman K. Page
*Assistant Examiner*—Peter F. Kulkosky

*Attorney, Agent, or Firm*—Finnegan, Henderson, Farabow, Garrett & Dunner

[57] ABSTRACT

The use of ionene polymers as anthelmintics is described. A composition for the treatment of helminth infections in an animal comprising an effective amount of at least one ionene polymer and a physiologically acceptable carrier other than water is disclosed. Also disclosed is a method for the treatment of a helminth infection in an animal.

60 Claims, No Drawings

OTHER PUBLICATIONS

M. J. H. Cawdery et al., Production Effects of Liver Fluke in Cattle I. The Effects of Infection on Liveweight Gain, Feed Intake and Food Conversion Efficiency in Beef Cattle, 133 Brit. Vet. J. 133 (1977).

A. M. Dunn, Veterinary Helminthology, (2d. ed. 1978).

Sydney M. Finegold and William J. Martin, "Bailey and Scott's Diagnostic Microbiology", (6th ed., 1982), "Contents", xi–xiii.

Noel R. Krieg and John G. Holt, "Bergey's Manual of Systematic Bacteriology," (1984) 1, Contents: xxiii.

Roger Y. Stanier, Edward A. Adelberg, and John Ingraham, "The Microbial World," 4th ed., (New Jersey: Prentice-Hall, Inc.), Contents, vii–xvii.

A. Rembaum, "Biological Activity of Ionene Polymers," Applied Polymer Symposium No. 22, 299–317 (John Wiley & Sons, Inc., 1973).

W. K. Joklik et al., "Zinsser Microbiology," (Appleton & Lange, Connecticut) (1992), Contents, iii–v.

Technical Disclosures for: BUSAN® 77 Rev. Aug. 5, 1992.

Busan® 79 Rev. Aug. 23, 1991.

Busan® 1099 Rev. Oct. 4, 1991.

Busan® 1157 Rev. Jul. 21, 1991.

Technical Disclosures and Material Safety Data Sheets for: BUSAN® 1055 Rev. Dec. 6, 1991.

BL® 1090 Rev. May 14, 1992.

BL® 1155 Rev. Aug. 1, 1992.

IONENE POLYMERS AS ANTHELMINTICS IN ANIMALS

This invention relates to the use of ionene polymers as helmintics for the treatment of helminth infections in animals.

The disease or group of diseases described generally as helminthiasis is due to infection of an animal host with parasitic worms known as helminths. Helminthiasis is a prevalent and serious economic problem in livestock animals such as swine, sheep, horses, cattle, goats, and poultry. Helminthiasis is also a serious health risk to humans and companion animals such as dogs, cats and other pets.

Among the helminths, the group of worms described as nematodes causes widespread, and often times serious, infection in various species of animals. Several of the more common genera of nematodes infecting the digestive systems of the animals referred to above are Ascaris, Haemonchus, Oesophagostomum, Strongyloides, Syphacia, and Trichostrongylus. Certain of these, such as Oesophagostomum, attack primarily the intestinal tract, while others, such as Haemonchus, are more prevalent in the stomach.

The adverse economic impacts on agriculture of the parasitic infections known as helminthiases are well known. See, e.g., R. S. Morris et al., *Measurement and Evaluation of the Economic Effects of Parasitic Disease*, 6 Vet. Parasitology 165 (1980) (hereby incorporated by reference). Helminth infections interfere with animal digestion and thus cause anemia, malnutrition, weakness, and weight loss. Helminths can also cause severe damage to the walls of the intestinal tract and other tissues and organs and, if left untreated, may result in death of the infected host animal. Accordingly, infected livestock will exhibit poor production performance as manifested by little or no weight gain, metabolic disturbances, sexual cycle abnormalities, and reduced milk production and quality.

Parasitic infections detract also from the quality of human and companion animal life. The impact on humans is particularly severe in third world nations. Helminthiasis causes similar symptoms in humans and companion animals to those found in livestock, including nausea, diarrhea, anemia, malnutrition, weight loss, weakness, and, in severe cases, death.

The invention provides a composition useful in treating helminth infections in animals.

The invention also provides a method for the treatment of helminth infections in animals.

Additionally, the invention prevents the loss of production performance of livestock and other domestic animals due to helminth infections.

Further, the invention improves the health and well-being of companion animals or humans by preventing or treating helminth infections.

The above aspects of the invention are accomplished by a composition for the treatment of helminth infections in animals comprising an effective amount of at least one ionene polymer and at least one physiologically acceptable ingredient other than water. Those aspects are also accomplished by a method for the treatment of a helminth infection in an animal comprising the step of administering to an animal in recognized need thereof an effective amount of at least one ionene polymer.

The present invention, therefore, relates to a composition for the treatment of helminth infections in mammals comprising an effective amount of an ionene polymer and a physiologically acceptable ingredient other than water. Ionene polymers or polymeric quaternary ammonium compounds, i.e., cationic polymers containing quaternary nitrogens in the polymer backbone (also known as polymeric quats or polyquats), belong to a well-known class of compounds. The biological activity of this class of polymers is also known. See, e.g., A. Rembaum, *Biological Activity of Ionene Polymers*, Applied Polymer Symposium No. 22, 299–317 (1973). Ionene polymers have a variety of uses in aqueous systems such as microbicides, bactericides, algicides, sanitizers, and disinfectants. U.S. Pat. Nos. 3,874,870, 3,931,319, 4,027,020, 4,089,977, 4,111,679, 4,506,081, 4,581,058, 4,778,813, 4,970,211, 5,051,124, and 5,093,078, which are incorporated here by reference, give various examples of these polymers and their uses. Ionene polymers have not, however, previously been known to treat helminth infections.

Ionene polymers may be classified according to the repeating unit found in the polymer. This repeating unit results from the reactants used to make the ionene polymer.

A first type of ionene polymer comprises the repeating unit of formula I:

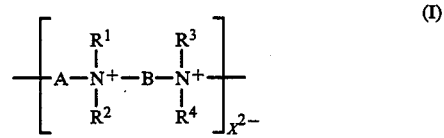

(I)

In this formula, $R^1$, $R^2$, $R^3$, and $R^4$ can be identical or different, and are selected from H, $C_1$–$C_{20}$ alkyl optionally substituted with at least one hydroxyl group, and benzyl optionally substituted on the benzene moiety with at least one $C_1$–$C_{20}$ alkyl group. Preferably, $R^1$, $R^2$, $R^3$ and $R^4$ are all methyl or ethyl.

The group "A" is a divalent radical selected from $C_1$–$C_{10}$ alkyl, $C_2$–$C_{10}$ alkenyl, $C_2$–$C_{10}$ alkynyl, $C_1$–$C_{10}$ hydroxyalkyl, symmetric or asymmetric di-$C_1$–$C_{10}$-alkylether, aryl, aryl-$C_1$–$C_{10}$-alkyl, or $C_1$–$C_{10}$-alkylaryl-$C_1$–$C_{10}$ alkyl. Preferably, "A" is $C_1$–$C_5$ alkyl, $C_2$–$C_5$ alkenyl, $C_2$–$C_5$ hydroxyalkyl, or symmetric di-$C_2$–$C_5$-alkylether, and most preferably "A" is —$CH_2CH_2CH_2$—, —$CH_2CH(OH)CH_2$- or —$CH_2CH_2OCH_2CH_2$—.

The group "B" is a divalent radical selected from $C_1$–$C_{10}$ alkyl, $C_2$–$C_{10}$ alkenyl, $C_2$–$C_{10}$ alkynyl, $C_1$–$C_{10}$ hydroxyalkyl, aryl, aryl-$C_1$–$C_{10}$-alkyl, or $C_1$–$C_{10}$-alkylaryl-$C_1$–$C_{10}$-alkyl. Preferably, "B" is $C_1$–$C_5$ alkyl, $C_2$–$C_5$ alkenyl, $C_2$–$C_5$ hydroxyalkyl, aryl, aryl-$C_1$–$C_5$-alkyl, or $C_1$–$C_5$ alkylaryl-$C_1$–$C_5$ alkyl. Most preferably "B" is —$CH_2CH_2$—, —$CH_2CH_2CH_2$—, —$CH_2CH_2CH_2CH_2$—, or —$CH_2(CH_2)_4CH_2$—.

The counter ion, $X^{2-}$, is a divalent counter ion, two monovalent counter ions, or a fraction of a polyvalent counter ion sufficient to balance the cationic charge in the repeating unit which forms the ionene polymer backbone. Preferably, $X^{2-}$ is two monovalent anions selected from a halide anion and a trihalide anion and more preferably, chloride or bromide. Ionene polymers having trihalide counter ions are described in U.S. Pat. No. 3,778,476, the disclosure of which is incorporated here by reference.

The ionene polymers having the repeating unit of formula I may be prepared by a number of known methods. One method is to react a diamine of the formula $R^1R^2N$—B—$NR^1R^2$ with a dihalide of the formula X-A-X. Ionene polymers having this repeating unit and methods for their preparation are described, for example, in U.S. Pat. Nos. 3,874,870, 3,931,319, 4,025,627, 4,027,020, 4,506,081 and 5,093,078, the disclosures of which are incorporated here by reference. The biological activity of ionene polymers having the repeating unit of formula I is also described in these patents.

A second type of ionene polymer comprises the repeating unit of formula II:

$$\left[-A-\underset{\underset{R^2}{|}}{\overset{\overset{R^1}{|}}{N^+}}-\right] X^-  \quad \text{(II)}$$

In this formula II, the definitions of $R^1$, $R^2$, and A are the same as those defined above for formula I. $X^-$ is a monovalent counter ion, one half of a divalent counter ion, or a fraction of a polyvalent counter ion sufficient to balance the cationic charge of the repeating unit which forms the ionene polymer. $X^-$ may be, for example, a halide or trihalide anion, and $X^-$ is preferably chloride or bromide.

The ionene polymers having the repeating unit of formula II may be prepared by known methods. One method is to react an amine of the formula $R^1R^2N$ witch a haloepoxide such as epichlorohydrin. Ionene polymers having the repeating unit of formula II are described, for example, in U.S. Pat. Nos. 4,111,679 and 5,051,124, the disclosures of which are incorporated here by reference. The biological activity of ionene polymers having the repeating unit of formula II is also described in these patents.

A third type of ionene polymer comprises a repeating unit of formula III:

$$+R-B'+ \quad \text{(III)}$$

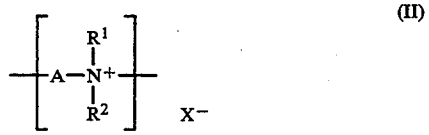

wherein R is

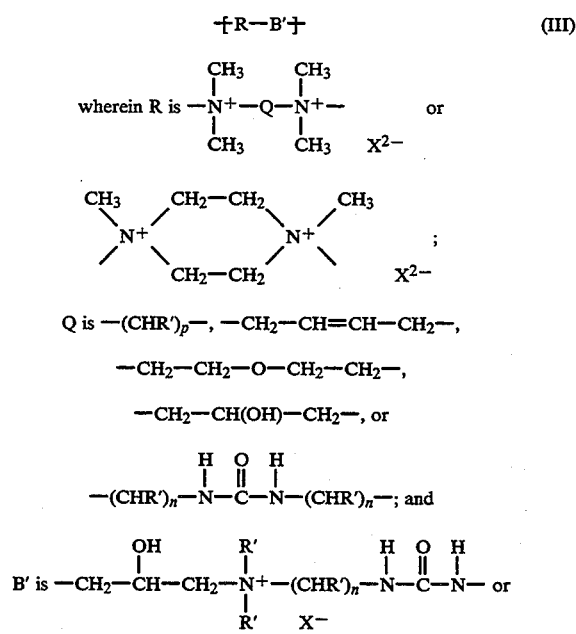

Q is —(CHR')$_p$—, —CH$_2$—CH=CH—CH$_2$—,

—CH$_2$—CH$_2$—O—CH$_2$—CH$_2$—,

—CH$_2$—CH(OH)—CH$_2$—, or $$-(CHR')_n-\underset{\underset{}{|}}{\overset{\overset{H}{|}}{N}}-\overset{\overset{O}{\|}}{C}-\underset{\underset{}{|}}{\overset{\overset{H}{|}}{N}}-(CHR')_n-; \text{ and}$$

B' is $$-CH_2-\overset{\overset{OH}{|}}{CH}-CH_2-\underset{\underset{R'}{|}}{\overset{\overset{R'}{|}}{N^+}}-(CHR')_n-\overset{\overset{H}{|}}{N}-\overset{\overset{O}{\|}}{C}-\overset{\overset{H}{|}}{N} \text{ or}$$
$$X^-$$

-continued
$$-(CHR')_n-\underset{\underset{R'}{|}}{\overset{\overset{R'}{|}}{N^+}}-CH_2-\overset{\overset{OH}{|}}{CH}-CH_2-;$$
$$X^-$$

n and p independently vary from 2 to 12; each R' is independently hydrogen or a lower alkyl group; $X^{2-}$ is a divalent counter ion, two monovalent counter ions, or a fraction of a polyvalent counter ion sufficient to balance the cationic charge in the group R; and $X^-$ is a monovalent counter ion, one half of a divalent counter ion or a fraction of a polyvalent counter ion sufficient to balance the cationic charge in the group B'. Preferably, R' is hydrogen or $C_1$-$C_4$ alkyl, n is 2-6, and p is 2-6. Most preferably, R' is hydrogen or methyl, n is 3 and p is 2. Preferred counter ions for $X^{2-}$ and $X^-$ are the same as those discussed above for formulae I and II.

The polymers of formula III are derived by known methods from bis-(dialkylaminoalkyl) ureas, which are also known as urea diamines. Ionene polymers of the formula III, methods of their preparation, and their biological activities are described in U.S. Pat. No. 4,506,081, the disclosure of which is incorporated here by reference.

Ionene polymers comprising the repeating units of formulae I, II, and III may also be cross-linked with primary, secondary or other polyfunctional amines using means known in the art. Ionene polymers can be cross-linked either through the quaternary nitrogen atom or through another functional group attached to the polymer backbone or to a side chain.

Cross-linked ionene polymers, prepared using cross-linking coreactants, are disclosed in U.S. Pat. No. 3,738,945 and Reissue U.S. Pat. No. 28,808, the disclosures of which are incorporated here by reference. The Reissue Patent describes the cross-linking of ionene polymers prepared by the reaction of dimethylamine and epichlorohydrin. The cross-linking coreactants listed are ammonia, primary amines, alkylenediamines, polyglycolamines, piperazines, heteroaromatic diamines and aromatic diamines.

U.S. Pat. No. 5,051,124, the disclosure of which is incorporated here by reference, describes cross-linked ionene polymers resulting from the reaction of dimethylamine, a polyfunctional amine, and epichlorohydrin. U.S. Pat. No. 5,051,124 also describes methods of inhibiting the growth of microorganisms using such cross-linked ionene polymers.

Other examples of various cross-linked ionene polymers and their properties are provided in U.S. Pat. Nos. 3,894,946, 3,894,947, 3,930,877, 4,104,161, 4,164,521, 4,147,627, 4,166,041, 4,606,773, and 4,769,155. The disclosures of each of these patents is incorporated here by reference.

The ionene polymers comprising the repeating units of formulae I, II, or III may also be capped, i.e., have a specific amino end group. Capping may be achieved by means known in the art. For example, an excess of either reactant used to make the ionene polymer can be employed to provide a capping group. Alternatively, a calculated quantity of a monofunctional tertiary amine or monofunctional substituted or unsubstituted alkyl halide can be reacted with an ionene polymer to obtain a capped ionene polymer. Ionene polymers can be capped at one or both ends. Capped ionene polymers and their microbicidal properties are described in U.S.

Pat. Nos. 3,931,319 and 5,093,078, the disclosures of which are incorporated here by reference.

Among the ionene polymers discussed above, a particularly preferred ionene polymer having a repeating unit of formula I is poly[oxyethylene(dimethyliminio)ethylene(dimethyliminio)ethylene dichloride. In this ionene polymer $R^1$, $R^2$, $R^3$ and $R^4$ are each methyl, A is —$CH_2CH_2OCH_2CH_2$—, B is —$CH_2CH_2$—, and $X^{2-}$ is $2Cl^-$, and the average molecular weight is 1,000–5,000. This ionene polymer is available from Buckman Laboratories, Inc. of Memphis, Tennessee as Busan® 77 product or WSCP® product, which are each 60% aqueous dispersions of the polymer. Busan® 77 and WSCP® are biocides used primarily in aqueous systems, including metalworking fluids, for microorganism control.

Another particularly preferred ionene polymer having a repeating unit of formula I is the ionene polymer where $R^1$, $R^2$, $R^3$ and $R^4$ are each methyl, A is —$CH_2CH(OH)CH_2$—, B is —$CH_2CH_2$—, and $X^{2-}$ is $2Cl^-$. This ionene polymer is a reaction product of N,N,N',N'-tetramethyl-1,2-ethanediamine with (chloromethyl)oxirane, and has an average molecular weight of 1,000–5,000. The polymer is available from Buckman Laboratories, Inc. as Busan® 79 product and WSCP® II product, which are each 60% aqueous solutions of the polymer.

Preferred ionene polymers having the repeating unit of formula II are those where $R^1$ and $R^2$ are each methyl, A is —$CH_2CH(OH)CH_2$—, and $X^-$ is $Cl^-$. This polymer is obtained as a reaction product of N-dimethylamine with (chloromethyl)oxirane, and has an average molecular weight of 2,000–10,000. The polymer is available from Buckman Laboratories, Inc. as the Busan® 1055 product, a 50% aqueous dispersion of the polymer.

Another preferred ionene polymer having the repeating unit of formula II is obtained as a reaction product of dimethylamine with epichlorohydrin, cross-linked with ethylenediamine, where R and $R^2$ are each methyl, A is —$CH_2CH(OH)CH_2$— and $X^-$ is $Cl^-$. This ionene polymer has a 100,000–500,000 average molecular weight, and is available from Buckman Laboratories, Inc. in a 50% aqueous dispersion as the Busan® 1157 product.

Another preferred ionene polymer having the repeating unit of formula II, where $R^1$ and $R^2$ are each methyl, A is —$CH_2CH(OH)CH_2$—, $X^-$ is $Cl^-$ and the ionene polymer is cross-linked with ammonia. This ionene polymer has a molecular weight of approximately 100,000–500,000, and is available from Buckman Laboratories, Inc. in a 50% aqueous dispersion sold as the Busan® 1155 product.

Buckman Laboratories, Inc. products BL® 1099 or Bubond® 65 are 25% aqueous dispersions of a cross-linked ionene polymer having repeating units of formula II, where $R^1$ and $R^2$ are each methyl, A is —$CH_2CH(OH)CH_2$—, $X^-$ is $Cl^-$, and the cross-linking agent is monomethylamine. This preferred ionene polymer has a molecular weight of approximately 10,000–100,000.

Preferred ionene polymers having the repeating unit of formula III are those where R is urea diamine and B' is $CH_2CH(OH)CH_2$, and $X^-$ is $Cl^-$. Available from Buckman Laboratories, Inc., ASTAT product and BL® 1090 product are 50% aqueous dispersions of this ionene polymer. The ionene polymer is obtained as a reaction product of N,N'-bis-[1-(3-(dimethylamino)propyl)] urea and epichlorohydrin, such ionene polymer having an average molecular weight of 2,000–15,000, preferably 3,000–7,000.

It has been found that ionene polymers can provide excellent effectiveness against helminth infections caused by nematodes in animals such as livestock and companion animals. The animal studies described below in the Examples also indicate that ionene polymers can successfully be used in the treatment of helminth infections in humans.

Ionene polymers effectively treat infections of helminths from the order Strongylida, particularly those helminths of the superfamilies Ascaridoidea, Oxyuroidea, Strongyloidea, and Trichostrongyloidea. More particularly, ionene polymers are useful in the treatment of infections caused by the helminths of the families Ascarididae, Trichonematidae, and Trichostrongylidae; the subfamily Oesophagostomatinae; and even more particularly, helminths of the genera Ascaris, Haemonchus, Oesophagostomum, Syphacia, and Trychostrongylus. Most particularly, ionene polymers are efficacious against the helminths Ascaris suum, Oesophagostomum dentatum, Oesophagostomum quadrispinulatum, Syphacia muris, and Trichostrongylus columbriformis.

Ionene polymers also can treat effectively infections by helminths of the order Rhabditida, particularly helminths of the superfamily Rhabditoidea, more particularly helminths of the family Strongyloididae, even more particularly helminths of the genus Strongyloides, and most particularly Strongyloides ransomi.

Ionene polymers also can treat effectively infections by helminths of the order Spirurida, particularly helminths of the superfamily Filarioidea, more particularly helminths of the family Onchocercidae, even more particularly helminths of the genus Dirofilaria, and most particularly Dirofilaria immitis (heartworm).

As indicated above, ionene polymers are effective for treating helminth infections in a variety of host animals, including companion animals and livestock. Companion animals include dogs, cats, and horses, as well as less common companion animals such as rodents, birds, and reptiles. Livestock animals include monogastrics such as pigs, horses, and poultry, and polygastrics or ruminants such as cattle, sheep, and goats.

According to one embodiment of this invention, at least one ionene polymer is present in a composition for the treatment of helminth infections in animals in an amount effective to treat helminthiasis, that is, to control the growth or proliferation of nematodes which cause helminthiasis. Under one regimen, the effective amount includes the amount of ionene polymer required to cure or rid an animal of a helminth infection or to decrease the nematode population to an acceptable level not endangering the health of the animal or the desired productivity, in the case of commercial livestock. According to this embodiment, ionene polymers may also be used in a second regimen to prospectively prevent helminth infections. Under this prophylactic treatment, an effective amount of the ionene polymer may be less than that required to cure or reduce an existing infection, but is an amount effective to prevent helminth infections from occurring. Under either of the above regimens, the ionene polymer may be administered in one or more doses.

A second embodiment of the invention, therefore, relates to a method for the treatment of a helminth infection in an animal comprising the step of administering to an animal in recognized need thereof an effective amount of at least one ionene polymer. This method may be employed in a treatment regimen to cure or rid an animal of a helminth infection or to decrease the nematode population to an acceptable level. This method may also be employed as a prophylactic regimen to prevent helminth infections in animals. As to the step of administering, the ionene polymer may be administered in a variety of ways as are known in the art.

The ionene polymers may be administered orally or, in the case of heartworm, intravenously. Oral administration can be in a unit dosage form such as a pellet, tablet, or capsule, or as a liquid drench. The drench is normally a solution, suspension, or dispersion of the active ingredient, usually in water, together with a suspending agent such as bentonite and a wetting agent or like excipient. Ethanol is also a suitable solvent. Generally, the drenches also contain an antifoaming agent. The pellets, tablets, or capsules comprise the active ingredient admixed with a physiologically acceptable ingredient vehicle such as starch, talc, magnesium stearate, or di-calcium phosphate.

By physiologically acceptable ingredient is meant one that will not adversely interact with, particularly not react with, the anthelmintic agent and one that may be administered safely to host animals. Physiologically acceptable ingredients specifically contemplated for use with this invention are those commonly used in veterinary and pharmaceutical practices, including, but not limited to, carriers or aids to make the polymers more acceptable to a host animal, flavoring agents, texture agents, odor control agents, adjuvants for other treatments including, but not limited to, vitamins, medicines, medicated or vitamin-enhanced food, weight gain enhancers, other health aids, or any ingredients generally included in food or water for animals.

Where it is desired to administer the ionene polymers in unit dosage form, pellets, tablets, or capsules containing the desired amount of active compound may be employed. These dosage forms are preferably prepared by intimately and uniformly mixing the active ingredient with suitable inert diluents, fillers, disintegrating agents and/or binders. Such unit dosage formulations may be varied widely with respect to their total weight and content of the antiparasitic agent depending upon factors such as the type of host animal to be treated, the severity and type of infection, and the weight of the host.

When the active compound is to be administered via an animal feedstuff, it is preferably intimately dispersed in the feed or used as a top dressing. The compound can also be administered in the form of pellets which are added to the finished feed or optionally fed separately. The compounds of the invention can also be incorporated into an animal mineral block. Alternatively, the anthelmintic compounds of the invention may be administered to animals parenterally, for example, by intraruminal injection, in which event the active ingredient may be dissolved or dispersed in a liquid carrier vehicle. For parenteral administration, the active material may be suitably admixed with a physiologically acceptable vehicle.

When the ionene polymer or a mixture of ionene polymers is administered as a component of the feed or drink of the animals, the ionene polymer or polymers may be dissolved or suspended in drinking water. Alternatively, compositions may be provided in which the ionene polymer or polymers are dispersed, preferably intimately, in an inert carrier or diluent. Preferably, a carrier for feed administration is one that is, or may be, an ingredient of the animal ration.

Representative compositions include feed premixes or supplements in which the active ingredient or ingredients are present in relatively large amounts and which are suitable for direct feeding to the animal or for addition to the feed either directly or after an intermediate dilution or blending step. Examples of carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone, and the like. The active ionene polymers are intimately dispersed throughout the carrier by methods such as grinding, stirring, milling, or tumbling.

Feed supplements containing effective amounts of the ionene polymers may be added to the animal feed in an amount to give the finished feed the concentration of active compound desired for the treatment and control of parasitic diseases. The desired concentration of active compound will vary depending upon the factors previously mentioned as well as upon the particular helminth infection treated and the particular ionene polymer employed.

In practicing this invention, individual ionene polymers may be prepared and used. Alternatively, mixtures of two or more individual polymers may be used, as well as mixtures of the polymers and other active compounds not related to the compounds of this invention.

Other anthelmintics or methods of treating helminth infections can be combined with the various treatments of helminth infections using ionene polymers according to this invention. The other anthelmintics or methods can be administered separately or in combination with an ionene polymer to treat or prevent a given helminth infection. Use of the same type of treatment regimen for the ionene polymer and other anthelmintic is not required. The combination of other anthelmintics or methods with ionene polymer treatment or prophylaxis can have additive or even synergistic efficacy in treating a helminth infection. Examples of such other anthelmintics are fenbendazole, oxfendazole, or the Ivermectin ® class of avermectins, available from Merck & Co.

The following examples are provided in order that this invention might be more fully understood; they are not to be construed as limitative of the invention.

EXAMPLE 1

Anthelmintic Efficacy Confirmation in Rats

Outbred rats, found to be infected with syphacia muris, were selected for study of five potential anthelmintic compounds. Ninety eight rats were divided into eight groups and identified with ionene polymers as follows: Group 1-Busan ® 77, Group 2-Busan ® 1055, Group 3-Busan ® 1099, Group 4-Busan ® 1157, Group 5-ASTAT. Groups 6 and 7 were used a negative controls and treated with water. Group 8 was used as a positive control and treated with piperazine. All animals were dosed by a gavage tube with one treatment per day for four days. Efficacy was determined by standard necropsy and worm counting protocols. Dose rates and efficacy results are shown in the Table I below.

TABLE I

| Group Number | Compound | Dose (mg/kg/day) | Efficacy |
|---|---|---|---|
| 1 | Busan ® 77 | 500 | 90.1% |
| 2 | Busan ® 1055 | 1000 | 94.0% |
| 3 | Busan ® 1099 | 1000 | 37.9% |
| 4 | Busan ® 1157 | 1000 | 93.3% |
| 5 | ASTAT | 250 | 12.7% |
| 6 | water | — | — |
| 7 | water | — | — |
| 8 | piperazine | 1000 | 65.0% |

EXAMPLE 2

Anthelmintic Efficacy Confirmation in Swine: Study 1

Forty four crossbred pigs were selected and individually marked for treatment with three experimental compounds. Each pig was infected with cultures of *Ascaris suum.*, *Strongyloides ransomi*, *Oesophagostomum spp.*, and *Trichuris suis*. Five treatment groups were established: three for experimental compounds, one for a negative control, and one for a positive control. Treatments were administered on feed for a total of three treatments over three days. Evaluation of efficacy was determined after necropsy according to standard methods. Efficacy results are given in the Table II below:

TABLE II

| Treatment | Dose mg/kg/day | Ascaris | Strongyloides | Oesophagostomum |
|---|---|---|---|---|
| Busan ® 77 | 500 | 51.6% | 92.2% | 67.6% |
| Busan ® 1055 | 1,000 | 62.4% | 74.7% | 85.6% |
| Busan ® 1157 | 1,000 | 0% | 65.8% | 75.1% |
| Fenbendazole | not reported | 92.6% | 63.3% | 100.0% |
| Control | — | 0% | 0% | 0% |

EXAMPLE 3

Anthelmintic Efficacy Confirmation in Swine: Study 2

A study was conducted as that described in Example 2 except that the treatment was for seven days. The efficacy results are given in Table III below::

TABLE III

| Treatment | Dose (mg/kg/day) | Ascaris | Strongyloides | Trichuris | Oesophagostomum |
|---|---|---|---|---|---|
| Busan ® 77 | 506 | 65.2% | 99.6% | 100% | 100% |
| Busan ® 1055 | 491 | 22.0% | 91.4% | 1004 | 100% |
| Busan ® 1157 | 593 | 48.8% | 52.8% | 99.6% | 99.7% |
| Fenbendazole | 1.5 | 100% | 47.6% | 100% | 100% |

EXAMPLE 4

Anthelmintic Efficacy Confirmation in Cattle

Thirty crossbred mixed sex beef calves were selected and individually marked for treatment with three experimental compounds. Each calve was infected with approximately 10,000 mixed species larvae (Ostertagia, Haemonchus, Trichostrongylus, Cooperia and Oesophagostomum). Five treatment groups were established: three for experimental compounds, one for a negative control, and one for a positive control. Treatments were administered orally for five consecutive days. Evaluation of efficacy was determined using standard fecal count methods. Efficacy results are given in the Table IV below:

TABLE IV

| | Fecal Egg Count Data | | |
|---|---|---|---|
| Treatment | Dose mg/kg/day | Egg Count | Efficacy |
| Busan ® 1157 | 730 | 42 | 96.3% |
| Busan ® 1055 | 650 | 241 | 78.9% |
| Busan ® 77 | 480 | 120 | 80.5% |
| Oxfendazole | 4.5 | 0 | 100.0% |
| Control | — | 1140 | NA |

$$\text{Efficacy} = \frac{\text{Control Eggs per Gram of Feces} - \text{Treated Eggs per Gram of Feces}}{\text{Control Eggs per Gram of Feces}} \times 100$$

The claimed invention is:

1. A composition for the treatment of helminth infections in an animal comprising an effective amount of at least one ionene polymer and at least one physiologically acceptable ingredient other than water, wherein said ionene polymer comprises a repeating unit of the formula I:

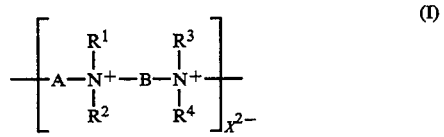

wherein $R^1$, $R^2$, $R^3$, and $R^4$ can be identical or different, and are selected from H, $C_1$–$C_{20}$ alkyl optionally substituted with at least one hydroxyl group, and benzyl optionally substituted on the benzene moiety with at least one $C_1$–$C_{20}$ alkyl group;

A is a divalent radical selected from $C_1$–$C_{10}$ alkyl, $C_2$–$C_{10}$ alkenyl, $C_2$–$C_{10}$ alkynyl, $C_1$–$C_{10}$ hydroxyalkyl, symmetric or asymmetric di-$C_1$–$C_{10}$-alkylether, aryl, aryl-$C_1$–$C_{10}$-alkyl, or $C_1$–$C_{10}$-alkylaryl-$C_1$–$C_{10}$-alkyl;

B is a divalent radical selected from $C_1$–$C_{10}$ alkyl, $C_2$–$C_{10}$ alkenyl, $C_2$–$C_{10}$ alkynyl, $C_1$–$C_{10}$ hydroxyalkyl, aryl, aryl-$C_1$–$C_{10}$-alkyl, or $C_1$–$C_{10}$-alkylaryl-$C_1$–$C_{10}$-alkyl; and $X^{2-}$ is a divalent counter ion, two monovalent counter ions or a fraction of a polyvalent counter ion sufficient to balance the cationic charge in the repeating unit of said ionene polymer.

2. The composition of claim 1, wherein $R^1$, $R^2$, $R^3$, and $R^4$ are methyl or ethyl; A is $C_1$–$C_5$ alkyl, $C_2$–$C_5$ alkenyl, $C_2$–$C_5$ hydroxyalkyl, or symmetric di-$C_2$–$C_5$-alkylether; B is $C_1$–$C_5$ alkyl, $C_2$–$C_5$ alkenyl, $C_2$–$C_5$ hydroxyalkyl, aryl, aryl-$C_1$–$C_5$-alkyl, or $C_1$–$C_5$ alkylaryl-$C_1$–$C_5$-alkyl; and $X^{2-}$ is two monovalent anions each selected from a halide anion or a trihalide anion.

3. The composition of claim 2, wherein A is —$CH_2CH_2CH_2$—, —$CH_2CH(OH)CH_2$— or —$CH_2CH_2OCH_2CH_2$—; B is —$CH_2CH_2$—, —$CH_2CH_2CH_2$—, —$CH_2CH_2CH_2CH_2$—, or —$CH_2(CH_2)_4CH_2$—; and $X^{2-}$ is $2Cl^-$.

4. The composition of claim 2, wherein $R^1$, $R^2$, $R^3$, and $R^4$ are —$CH_3$; B is —$CH_2CH_2$—; and A is —$CH_2CH(OH)CH_2$—.

5. The composition of claim 2, wherein $R^1$, $R^2$, $R^3$, and $R^4$ are each methyl, A is —$CH_2CH_2OCH_2CH_2$— and B is —$CH_2CH_2$—.

6. The composition of claim 2, wherein said ionene polymer is a cross-linked polymer.

7. A composition for the treatment of helminth infections in an animal comprising an effective amount of at least one ionene polymer and at least one physiologically acceptable ingredient other than water, wherein said ionene polymer comprises a repeating unit of formula II:

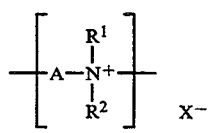

wherein $R^1$ and $R^2$ can be identical or different, and are selected from H, $C_1$–$C_{20}$ alkyl optionally substituted with at least one hydroxyl group, and benzyl optionally substituted on the benzene moiety with at least one $C_2$–$C_{20}$ alkyl group;

A is a divalent radical selected from $C_1$–$C_{10}$ alkyl, $C_2$–$C_{10}$ alkenyl, $C_2$–$C_{10}$ alkynyl, $C_1$–$C_{10}$ hydroxyalkyl, symmetric or asymmetric di-$C_1$–$C_{10}$-alkylether, aryl, aryl-$C_1$–$C_{10}$-alkyl, or $C_1$–$C_{10}$-alkylaryl-$C_1$–$C_{10}$-alkyl; and $X^-$ is a monovalent counter ion, one-half of a divalent counter ion or a fraction of a polyvalent counter ion sufficient to balance the cationic charge of the repeating unit in said ionene polymer.

8. The composition of claim 7, wherein $R^1$ and $R^2$ may be the same or different and are methyl or ethyl; A is $C_1$–$C_5$ alkyl, $C_2$–$C_5$ alkenyl, $C_2$–$C_5$ hydroxyalkyl, or symmetric di-$C_2$–$C_5$-alkylether; and $X^-$ is a halide anion.

9. The composition of claim 8, wherein A is —$CH_2CH_2CH_2$—, —$CH_2CH(OH)CH_2$—, or —$CH_2CH_2OCH_2CH_2$—; and $X^-$ is $Cl^-$.

10. The composition of claim 8, wherein $R^1$ and $R^2$ are each methyl, and A is —$CH_2CH(OH)CH_2$—.

11. The composition of claim 8, wherein $R^1$ and $R^2$ are each methyl, and A is —$CH_2CH(OH)CH_2$— and said ionene polymer is cross-linked with ethylenediamine.

12. The composition of claim 8, wherein $R^1$ and $R^2$ are each methyl, A is —$CH_2CH(OH)CH_2$—, and said ionene polymer is cross-linked with ammonia.

13. The composition of claim 8, wherein $R_1$ and $R_2$ are each methyl, A is —$CH_2CH(OH)CH_2$—, $X^-$ is $Cl^-$, and said ionene polymer is cross-linked with monomethylamine.

14. The composition of claim 7, wherein said ionene polymer is a cross-linked polymer.

15. A composition for the treatment of helminth infections in an animal comprising an effective amount of at least one ionene polymer and at least one physiologically acceptable ingredient other than water, wherein said ionene polymer comprises a repeating unit of formula III:

-continued

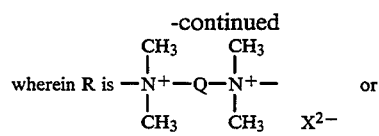

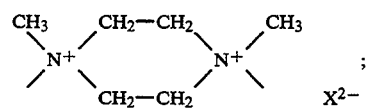

Q is —$(CHR')_p$—, —$CH_2$—$CH$=$CH$—$CH_2$—,

—$CH_2$—$CH_2$—$O$—$CH_2$—$CH_2$—,

—$CH_2$—$CH(OH)$—$CH_2$—, or

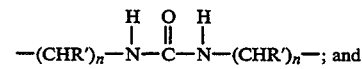

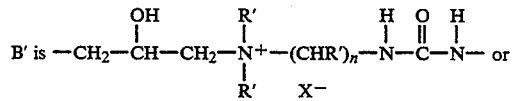

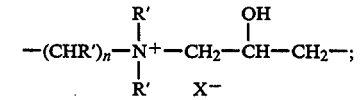

wherein n and p vary independently from 2 to 12; each $R'$ is independently hydrogen or a lower alkyl group; $X^{2-}$ is a divalent counter ion, two monovalent counter ions or a fraction of a polyvalent counter ion sufficient to balance the cationic charge in said group R; and $X^-$ is a monovalent counter ion, one-half of a divalent counter ion or a fraction of a polyvalent counter ion sufficient to balance the cationic charge in said group B'.

16. The composition of claim 15, wherein $R'$ is hydrogen or $C_1$–$C_4$, n is 2–6, and p is 2–6.

17. The composition of claim 15, wherein $R'$ is hydrogen or methyl, n is 3, and p is 2.

18. The composition of claim 15, wherein R is urea diamine, B' is —$CH_2CH(OH)CH_2$—, and X' is $Cl^-$.

19. A method for the treatment of a helminth infection in an animal comprising the step of administering to an animal in recognized need thereof an effective amount of at least one ionene polymer, wherein said ionene polymer comprises a repeating unit of the formula I:

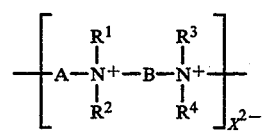

wherein $R^1$, $R^2$, $R^3$ and $R^4$ can be identical or different, and are selected from H, $C_1$–$C_{20}$ alkyl optionally substituted with at least one hydroxyl group, and benzyl optionally substituted on the benzene moiety with at least one $C_1$–$C_{20}$ alkyl group;

A is a divalent radical selected from $C_1$–$C_{10}$ alkyl, $C_2$–$C_{10}$ alkenyl, $C_2$–$C_{10}$ alkynyl, $C_1$–$C_{10}$ hydroxyalkyl, symmetric or asymmetric di-$C_1$–$C_{10}$-alkylether, aryl, aryl-$C_1$–$C_{10}$-alkyl, or $C_1$–$C_{10}$-alkylaryl-$C_1$–$C_{10}$-alkyl;

B is a divalent radical selected from $C_1$–$C_{10}$ alkyl, $C_2$–$C_{10}$ alkenyl, $C_2$–$C_{10}$ alkynyl, $C_1$–$C_{10}$ hydroxyalkyl, aryl, aryl-$C_1$–$C_{10}$-alkyl, or $C_1$–$C_{10}$-alkylaryl-$C_1$–$C_{10}$-alkyl; and $X^{2-}$ is a divalent counter ion, two monovalent counter ions or a fraction of a polyvalent counter ion sufficient to balance the cationic charge in the repeating unit of said ionene polymer.

20. The method of claim 19, wherein $R^1$, $R^2$, $R^3$, and $R^4$ are methyl or ethyl; A is $C_1$–$C_5$ alkyl, $C_2$–$C_5$ alkenyl, $C_2$–$C_5$ hydroxyalkyl, or symmetric di-$C_2$–$C_5$-alkylether; B is $C_1$–$C_5$ alkyl, $C_2$–$C_5$ alkenyl, $C_2$–$C_5$ hydroxyalkyl, aryl, aryl-$C_1$–$C_5$-alkyl, or $C_1$–$C_5$ alkylaryl-$C_1$–$C_5$-alkyl; and X is two monovalent anions each selected from a halide anion or a trihalide anion.

21. The method of claim 20, wherein A is —$CH_2CH_2CH_2$—, —$CH_2CH(OH)CH_2$— or —$CH_2CH_2OCH_2CH_2$—; B is —$CH_2CH_2$—, —$CH_2CH_2CH_2$—, —$CH_2CH_2CH_2CH_2$—, or —$CH_2(CH_2)_4CH_2$—; and $X^{2-}$ is $2Cl^-$.

22. The method of claim 20, wherein $R^1$, $R^2$, $R^3$, and $R^4$ are —$CH_3$, B is —$CH_2CH_2$—, and A is —$CH_2CH(OH)CH_2$—.

23. The method of claim 20, wherein $R^1$, $R^2$, $R^3$ and $R^4$ are each methyl, A is —$CH_2CH_2OCH_2CH_2$— and B is —$CH_2CH_2$—.

24. The method of claim 19 wherein said ionene polymer is a cross-linked polymer.

25. The method of claim 19, wherein said animal is a human.

26. The method of claim 19, wherein said animal is a companion animal.

27. The method of claim 26, wherein said companion animal is selected from dogs, cats, equine animals, birds, rodents, or reptiles.

28. The method of claim 19, wherein said animal is a livestock animal.

29. The method of claim 28, wherein said livestock animal is selected from cattle, swine, sheep, goats, equine animals, or poultry.

30. A method for the treatment of a helminth infection in an animal comprising the step of administering to an animal in recognized need thereof an effective amount of at least one ionene polymer, wherein said ionene polymer comprises a repeating unit of formula II:

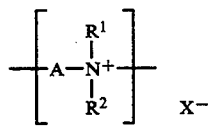

wherein $R^1$ and $R^2$ can be identical or different, and are selected from H, $C_1$–$C_{20}$ alkyl optionally substituted with at least one hydroxyl group, and benzyl optionally substituted on the benzene moiety with at least one $C_2$–$C_{20}$ alkyl group;

A is a divalent radical selected from $C_1$–$C_{10}$ alkyl, $C_2$–$C_{10}$ alkenyl, $C_2$–$C_{10}$ alkynyl, $C_1$–$C_{10}$ hydroxyalkyl, symmetric or asymmetric di-$C_1$–$C_{10}$-alkylether, aryl, aryl-$C_1$–$C_{10}$-alkyl, or $C_1$–$C_{10}$-alkylaryl-$C_1$–$C_{10}$-alkyl; and $X^-$ is a monovalent counter ion, one-half of a divalent counter ion or a fraction of a polyvalent counter ion sufficient to balance the cationic charge of the repeating unit in said ionene polymer.

31. The method of claim 30, wherein $R^1$ and $R^2$ may be the same or different and are methyl or ethyl; A is $C_1$–$C_5$ alkyl, $C_2$–$C_5$ alkenyl, $C_2$–$C_5$ hydroxyalkyl, or symmetric di-$C_2$–$C_5$-alkylether; and $X^-$ is a halide anion.

32. The method of claim 31, wherein A is —$CH_2CH_2CH_2$—, —$CH_2CH(OH)CH_2$—, or —$CH_2CH_2OCH_2CH_2$—; and $X^-$ is $Cl^-$.

33. The method of claim 31, wherein $R^1$ and $R^2$ are each methyl, and A is —$CH_2CH(OH)CH_2$—.

34. The method of claim 31, wherein $R^1$ and $R^2$ are each methyl, A is —$CH_2CH(OH)CH_2$—, and said ionene polymer is cross-linked with ethylenediamine.

35. The method of claim 31, wherein $R^1$ and $R^2$ are each methyl, A is —$CH_2CH(OH)CH_2$—, and said ionene polymer is cross-linked with ammonia.

36. The method of claim 31, wherein $R_1$ and $R_2$ are each methyl, A is —$CH_2CH(OH)CH_2$—, $X^-$ is $Cl^-$, and said ionene polymer is cross-linked with monomethylamine.

37. The method of claim 30, wherein said ionene polymer is a cross-linked polymer.

38. The method of claim 30, wherein said animal is a human.

39. The method of claim 30, wherein said animal is a companion animal.

40. The method of claim 39, wherein said companion animal is selected from dogs, cats, equine animals, birds, rodents, or reptiles.

41. The method of claim 30, wherein said animal is a livestock animal.

42. The method of claim 41, wherein said livestock animal is selected from cattle, swine, sheep, goats, equine animals, or poultry.

43. A method for the treatment of a helminth infection in an animal comprising the step of administering to an animal in recognized need thereof an effective amount of at least one ionene polymer, wherein said ionene polymer comprises a repeating unit of formula III:

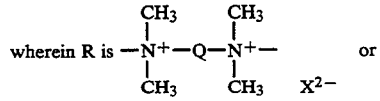

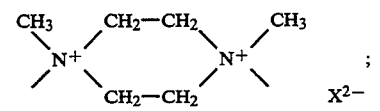

Q is —$(CHR')_p$—, —$CH_2$—$CH$=$CH$—$CH_2$—,

—$CH_2$—$CH_2$—$O$—$CH_2$—$CH_2$—,

—$CH_2$—$CH(OH)$—$CH_2$—, or

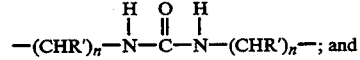

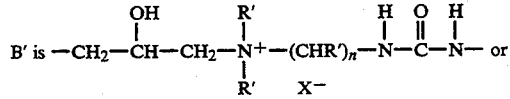

-continued

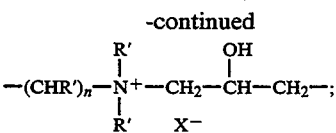

wherein n and p vary independently from 2 to 12; each R' is independently hydrogen or a lower alkyl group; $X^{2-}$ is a divalent counter ion, two monovalent counter ions or a fraction of a polyvalent counter ion sufficient to balance the cationic charge in said group R; and $X^-$ is a monovalent counter ion, one-half of a divalent counter ion or a fraction of a polyvalent counter ion sufficient to balance the cationic charge in said group B'.

44. The method of claim 43, wherein R' is hydrogen or $C_1$-$C_4$, n is 2-6, and p is 2-6.

45. The method of claim 43, wherein R' is hydrogen or methyl, n is 3, and p is 2.

46. The method of claim 43, wherein R is urea diamine, B' is $CH_2CH(OH)CH_2$, and $X^-$ is $Cl^-$.

47. The method of claim 44, wherein said animal is a human.

48. The method of claim 44, wherein said animal is a companion animal.

49. The method of claim 48, wherein said companion animal is selected from dogs, cats, equine animals, birds, rodents, or reptiles.

50. The method of claim 43, wherein said animal is a livestock animal.

51. The method of claim 50, wherein said livestock animal is selected from cattle, swine, sheep, goats, equine animals, or poultry.

52. The method of claim 19, 30 and 43, wherein said helminth infection is caused by helminths selected from the orders Strongylida or Rhabditida.

53. The method of claim 19, 30 and 43, wherein said helminth infection is caused by helminths selected from the superfamilies Ascaridoidea, Strongyloidea, Oxyuroidea, Trichostrongyloidea, or Rhabditoidea.

54. The method of claims 19, 30 and 43, wherein said helminth infection is caused by helminths selected from the families Ascarididae, Trichonematidae, Trichostrongylidae, or Strongyloididae, or the subfamily Oesophagostomatinae.

55. The method of claim 19, 30 and 43, wherein said helminth infection is caused by helminths selected from the genera Ascaris, Oesophagostomum, Syphacia, Trychostrongulus, Haemonchus, or Strongyloides.

56. The method of claim 19, 30 and 43, wherein said helminth infection is caused by helminths selected from the species Ascaris suum, Oesophagostomum dentatum,, Oesophagostomum quadrispinulatum, Syphacia muris, Trychostrongylus colubriformis, or Strongyloides ransomi.

57. The method of claim 19, 30 and 43, wherein said ionene polymer is administered in a composition comprising at least one ionene polymer and at least one physiologically acceptable ingredient other than water.

58. The method of claim 19, wherein said ionene polymer is administered in a composition comprising at least one ionene polymer and at least one physiologically acceptable ingredient other than water.

59. The method of claim 30, wherein said ionene polymer is administered in a composition comprising at least one ionene polymer and at least one physiologically acceptable ingredient other than water.

60. The method of claim 43, wherein said ionene polymer is administered in a composition comprising at least one ionene polymer and at least one physiologically acceptable ingredient other than water.

* * * * *

UNITED STATES PATENT AND TRADEMARK OFFICE
CERTIFICATE OF CORRECTION

PATENT NO. : 5,419,897
DATED : May 30, 1995
INVENTOR(S) : Kevin D. DRAKE et al.

It is certified that error appears in the above-indentified patent and that said Letters Patent is hereby corrected as shown below:

Claim 19, col. 13, line 8, "of-said" should read --of said--.

Claim 20, col. 13, line 14, "X" should read --$X^{2-}$--.

Claim 30, col. 14, line 1, ".charge" should read --charge--.

Claim 56, col. 16, line 20, ",," should read --,--.

Signed and Sealed this

Eighth Day of August, 1995

Attest:

BRUCE LEHMAN

*Attesting Officer*     *Commissioner of Patents and Trademarks*